US005490987A

United States Patent [19]

Shen et al.

[11] Patent Number: 5,490,987
[45] Date of Patent: Feb. 13, 1996

[54] TABLETING OF COLESTIPOL HYDROCHLORIDE

[75] Inventors: Robert W. Shen, Kalamazoo; Jeffrey E. Price, Schoolcraft, both of Mich.

[73] Assignee: The Upjohn Company, Kalamazoo, Mich.

[21] Appl. No.: 175,412

[22] PCT Filed: Jun. 23, 1992

[86] PCT No.: PCT/US92/05066

§ 371 Date: Dec. 30, 1993

§ 102(e) Date: Dec. 30, 1993

[87] PCT Pub. No.: WO93/00915

PCT Pub. Date: Jan. 21, 1993

Related U.S. Application Data

[63] Continuation-in-part of Ser. No. 725,044, Jul. 3, 1991, abandoned.

[51] Int. Cl.$^6$ .................... A61K 9/20; A61K 9/36
[52] U.S. Cl. .................. 424/464; 424/465; 424/480; 514/770; 514/772.3; 514/784; 514/824; 514/960; 514/961
[58] Field of Search .................. 424/464, 465, 424/480, 482

[56] References Cited

U.S. PATENT DOCUMENTS

| | | | |
|---|---|---|---|
| 3,692,895 | 9/1972 | Nelson et al. | 424/78 |
| 3,803,237 | 4/1974 | Lednicer et al. | 260/584 R |
| 4,404,346 | 9/1983 | Pirotta et al. | 521/29 |
| 4,439,419 | 3/1984 | Vecchio | 424/78 |
| 4,631,305 | 12/1986 | Guyer et al. | 523/400 |

FOREIGN PATENT DOCUMENTS

| | | | |
|---|---|---|---|
| 0026574 | 6/1980 | European Pat. Off. | A61K 9/14 |
| 0347748 | 6/1989 | European Pat. Off. | A61K 9/52 |
| WO89/12452 | 12/1989 | European Pat. Off. | A61K 31/785 |
| WO90/02148 | 3/1990 | European Pat. Off. | A61K 31/785 |

OTHER PUBLICATIONS

"Pharmaceutical Dosage Forms": Tablets, vol. 1, Edited by H. A. Lieberman and L. Lachman, Marcel Dekker, Inc., New York and Basel, pp. 114–116, 122–129 and 184–185, (1980).

USP XXII "Povidone", p. 1118, (1990).

"Remington's Pharmaceutical Sciences", RPS XIV, John E. Hoover, Managing Editor, 14th Edition, Mack Publishing Co. Pa., pp. 1655–1659, (1970).

Physicians' Desk Reference (PDR), 42nd Edition, 1988, p. 2115.

*Primary Examiner*—Thurman K. Page
*Assistant Examiner*—James M. Spear
*Attorney, Agent, or Firm*—Martha A. Gammill

[57] ABSTRACT

The present invention provides a novel formulation of matter and a novel process for making it. In particular, the present invention provides unique and novel 1000 mg tablets of Colestipol hydrochloride having the advantageous properties of hardness and low friability and a novel process for making such tablets.

17 Claims, No Drawings

TABLETING OF COLESTIPOL HYDROCHLORIDE

This application is the national phase a 371 of international application PCT/US92/05066 filed Jun. 23, 1992 which is a CIP of U.S. Ser. No. 07/725,044 filed 3 Jul. 1991, now abandoned.

BACKGROUND OF THE INVENTION

The present invention provides a novel formulation of matter and a novel process for making it. In particular, the present invention provides unique and novel high potency (e.g. 1000 mg) tablets of colestipol hydrochloride having the advantageous properties of hardness, friability and thickness, and a novel process for making such tablets.

Colestipol is a basic anion exchange resin described as a high molecular weight copolymer of diethylenetriamine and 1-chloro-2,3-epoxypropane (hydrochloride), with approximately 1 out of 5 amine nitrogens protonated. It may also be named as diethylenetriamine-epichlorohydrin copolymer, hydrochloride. It is a light yellow resin which is hygroscopic and swells when placed in water or aqueous fluids. See Merck Index (Tenth Edition) #2440, page 2438. Colestipol hydrochloride is commercially available in granule form as COLESTID® Granules. See Physicians Desk Reference (PDR) 42nd Ed., p. 2119 (1988).

COLESTID® Granules are marketed as a hyperlipidemia agent for oral use. COLESTID® Granules are tasteless and odorless, although they may have a pronounced gritty texture when suspended in liquids consumed orally.

Cholesterol is the major, and probably the sole precursor of bile acids. During normal digestion, bile acids are secreted via the bile from the liver and gall bladder into the intestines. Bile acids emulsify the fat and lipid materials present in food, thus facilitating absorption. A major portion of the bile acids secreted is reabsorbed from the intestines and returned via the portal circulation to the liver, thus completing an enterohepatic cycle. Only very small amounts of bile acids are found in normal serum. Physicians' Desk Reference (P.D.R.) 42nd Edition, 1988, page 2115.

Colestipol hydrochloride, sold, e.g., in COLESTID® Granules, is indicated as adjunctive therapy to diet for the reduction of elevated serum cholesterol in patients with primary hypercholesterolemia (elevated low density lipoproteins). These granules must be consumed orally and typically require admixture with a pleasant tasting vehicle at the time of oral consumption. The typical daily dose of COLESTID® Granules employed for anti-hypercholesterolemia varies from 15 to 30 grams per day. Patients taking this medication ordinarily must continue to take anti-cholesterolemic drugs throughout their lives to maintain reduced serum cholesterol levels.

However, COLESTID® Granules, are not well tolerated by patients since the gritty texture of the product is objectionable, severely compromising the pharmaceutical elegance and patient acceptance. Further, the use of a granule formulation means that drug must be mixed with a liquid vehicle at the time of consumption, an inconvenience for many patients. For example, in order to take this drug, patients must measure the powder, disperse it in a liquid vehicle and drink the entire contents. Therefore, a pharmaceutically more elegant and convenient dosage form of Colestipol hydrochloride is needed, such as a tablet.

INFORMATION DISCLOSURE

U.S. patent application Ser. No. 07/623,904, filed Dec. 19, 1990, now abandoned (which is also International Publication No. WO 89/12452, published 28 Dec. 1989) discloses fine-milled colestipol hydrochloride and tablets made therefrom. Some of the differences between these tablets and the tablets of the current invention are listed in Table 1. Table 2 shows some of the differences between the processes used to make these two different tablets.

According to Table 1, the tablets of the present invention are much harder than the prior art tablets, yet they disintegrate readily. Also, the tablets of the present invention are advantageously smaller than the prior art tablets. Other advantageous properties of the tablets of the present invention, such as friability and disintegration time, are also set forth in the Table.

According to Table 2, the process of the present invention utilizes a wet granulation method at the bulk drug stage rather than direct compression, thus avoiding repetitive drying of the material. The present process utilizes a one-step drying process whereas the prior art utilizes a two-step drying process. These and other differences are further exemplified below.

Pharmaceutical Dosage Forms: Tablets, Volume 1, Edited by H. A. Lieberman and L. Lachman (1980), Marcel Dekker, Inc., New York and Basel, pp. 114–116, 122–129, 184–185, includes a description of the wet granulation process which is a well known method for preparing granules for tableting. It is stated that it is the process of choice to use in tablet formulations of many high-dose drugs. It also describes a number of excipients such as binders, which are used in a tablet formulation in addition to the active ingredient. It lists the following as binders that are used in wet granulation: starch, pregelatinized starch, gelatin, polyvinylpyrrolidone, methylcellulose, sodium carboxymethylcellulose, ethylcellulose, polyacrylamides, polyvinyloxazolidone and polyvinyl alcohols. It states that the binder is fundamental to the granulation particle size uniformity, adequate hardness, ease of compression and general quality of the tablet.

Polyvinyl pyrrolidone, also known as PVP and Povidone, is a well known tablet binder and granulating excipient. USP XXII (1990) "Povidone" on page 1118.

Published European application 0 347,748 discloses a composition for coating drug granules which is made of a polymer, such as povidone, and microcrystalline cellulose. It states the belief that the polymer material functions as a binder and carrier for the microcrystalline cellulose, while the microcrystalline cellulose imparts the excellent compressibility properties to the granules.

Remington's Pharmaceutical Sciences, RPS XIV, John E. Hoover, Managing Editor, 14th Edition, (1970) Mack Publishing Co, Pa., pp. 1655–1659 describes the different steps and equipment that may be used in wet-granulation method for tablet preparation.

Colestipol hydrochloride in the form of spherical beads, wherein at least 75% of the particles by weight or volume are greater than 100 microns in diameter and 30% of the particles by weight or volume are greater than 80 microns in diameter, is known. See PDR, Supra, page 2115. The use of oral colestipol hydrochloride formulations in spherical bead form to treat hypercholesterolemia is also known. See, e.g., U.S. Pat. No. 3,692,895.

A fine-beaded form of Colestipol hydrochloride is disclosed in International Publication WO 90/02148, published 8 Mar. 1990.

U.S. Pat. No. 4,404,346 discloses and claims a process for reducing the size of particles of anti-hypercholesterolemic cholestyramine resins. Powdered cholestyramine resin is produced by swelling or shrinking resin particles by contact with water or an organic solvent to introduce strain within the particles and comminuting the swollen or shrunk particles by grinding them in a rotary attrition mill. Particle sizes such that 90% by weight and/or number is below 30 microns in average particle diameter in the wet swollen state are reported to have been achieved.

EP-B-0026574, claims a process for reducing the size of particles of synthetic polymeric ion exchange or adsorbent resins in general, and of cholestyramine specifically. It also claims the comminuted synthetic polymeric ion exchange or adsorbent resin obtained by this process, the comminuted cholestyramine obtained by this process, and the resins themselves in pharmaceutical formulations.

U.S. Pat. No. 3,692,895 claims a method of using colestipol hydrochloride to reduce hypercholesterolemia in humans. It discloses compositions (including tablets and capsules) and processes for reducing hypercholesterolemia in affected mammals and birds. The compositions and processes utilize an orally effective amount of a non-toxic polymer prepared from a polyethylenepolyamine such as tetraethylenepentamine and a bifunctional substance such as epichlorohydrin or 1,2:3,4-diepoxybutane.

U.S. Pat. No. 4,439,419 discloses a method of using colestipol hydrochloride to neutralize gastric acidity and treat hyperacidity in humans having an excess of gastric acidity and the treatment of ulcers.

A preferred method for preparing colestipol hydrochloride for medical use is disclosed in U.S. Pat. No. 3,803,237 and is known as the "bead process." U.S. Pat. No. 4,631,305 claims compressed tablets containing a polymeric material such as colestipol hydrochloride as a tablet disintegrating agent.

SUMMARY OF THE INVENTION

The present invention particularly provides:

A pharmaceutical tablet, which comprises:

a) one or more pharmaceutically acceptable excipients, and b) an amount of colestipol hydrochloride effective to treat or prevent hypercholesterolemia in a patient to whom one or more tablets are administered; which has the following physical characteristics:

| Hardness: | 40–75 SCUs |
| Thickness: | 0.200"–0.340" |
| Friability: | 0–0.1%/15 minutes; and |

A process for preparing a 1000 mg tablet of colestipol hydrochloride which comprises: adding povidone to a slurry of fine milled colestipol hydrochloride.

By "Hardness" is meant the measure of the force needed to fracture a tablet when such tablet is placed lengthwise on the Hardness Tester. It is measured in Strong Cobb Units (SCUs).

The "Friability" is the measure of the stability of the tablet needed to sustain the rolling action of a coating pan and packaging. It is measured at timed intervals, such as 15 minutes, in a Roche Friabulator.

By "Thickness" is meant the measure of the height of the tablet in inches, using a micrometer.

The "Disintegration Time" is the time necessary for the tablet to break apart in purified water (37° C.). It is measured in minutes.

By a "Slurry of Fine Milled Colestipol Hydrochloride" is meant a mixture of Colestipol hydrochloride beads and water, at a ratio of from 5 to 1 (water to beads) to a ratio of 12 to 1 (water to beads), which has been milled in a precision incremental cutting machine, such as a Comitrol mill, according to the process described in International Publication No. WO 89/12452, published 28 Dec. 1989, which is hereby incorporated by reference herein. The Colestipol hydrochloride beads are prepared by the "bead process" which is described in U.S. Pat. No. 3,803,237, which is hereby incorporated by reference herein, and may be utilized in the slurry in a dried state (e.g., Formula B-3 material in Chart B) or in a wet state (e.g., Formula A-3 material in Chart A), with the wet state being preferred. The beads may also be prepared by the "fine bead process" which is described in International Publication No. WO 90/02148, published 8 Mar. 1990, which is hereby incorporated by reference herein.

By "fine milled" is meant a substantially non-spherical form of colestipol hydrochloride (greater than 95% non-spherical, fractured particles, most preferably greater than about 99% non-spherical fractured particles) wherein greater than 75% of the particles by weight or volume are less than about 100 microns in diameter; more preferably greater than about 75% of the particles, by weight or volume, are less than about 65 microns in diameter and greater than about 30% of the particles (as a proportion of their total weight or volume), are less than about 30 microns in diameter. These measurements of diameter of particle size may be made by standard light scattering assay techniques. The "fine milled" form of colestipol hydrochloride is also described in International Publication No. WO 89/12452, published 28 Dec. 1989, as noted above.

By "Dewatered" is meant that water has been removed from the slurry by known conventional processes, down to a moisture content of 74–85%, and preferably 80%.

The preferred amount of colestipol hydrochloride per tablet of the present invention is 1000 mg. In hyperlipidemic patients with serum cholesterol values above 200 mg per 100 ml, the tablets of the present invention have been shown to effectively lower cholesterol levels. Current clinical data shows that two 10430 mg tablets administered to such patients twice daily lower cholesterol approximately 12% and eight 1000 mg tablets administered to such patients twice daily lower cholesterol approximately 24%.

The tablets of present invention also typically have the following additional physical characteristics: Tablet Weight: 1017 mg–1079 mg; and Disintegration Time: Less than 5 minutes. The tablets may be compressed and preferably have a tablet weight of approximately 1048 mg, a hardness of 40 to 50 SCUs, and a thickness of 0.320"–0.340".

The excipients which are preferred for use in the tablets of the present invention are povidone, colloidal silicon dioxide and magnesium stearate. The amounts of these excipients in the tablets of the present invention are from about 10 to about 200 mg of povidone, from about 1 to about 50 mg of colloidal silicon dioxide, and from about 1 to about 30 mg of magnesium stearate. The preferred amounts of these excipients are from about 40 to about 50 mg of povidone, from about 5 to about 10 mg of colloidal silicon dioxide, and from about 2.5 to about 3.5 mg of magnesium stearate, with approximately 40 mg of povidone, approximately 5 mg of colloidal silicon dioxide and approximately 3 mg of magnesium stearate, being most preferred.

The tablets of the present invention may further have a seal coating comprising cellulose acetate phthalate and triacetin. The amounts of these ingredients in the seal coating are from about 2 to about 100 mg of cellulose acetate phthalate and from about 0.5 to about 20 mg of triacetin, with approximately 15.6 mg of cellulose acetate phthalate and approximately 3.12 mg of triacetin, being most preferred.

The tablets of the present invention may also have a clear coating, in addition to the seal coating, comprising hydroxypropyl methylcellulose and triacetin. The amounts of these ingredients in the clear coating are from about 5 to about 100 mg of hydroxypropyl methylcellulose 2910 E5 Premium USP 5 CPS, from about 5 to about 100 mg of hydroxypropyl methylcellulose 2910 USP 15 CPS and from about 2 to about 80 mg of triacetin, with approximately 30 mg of hydroxypropyl methylcellulose 29 10 E5 Premium USP 5 CPS, approximately 30 mg of hydroxypropyl methylcellulose 2910 USP 15 CPS and approximately 12 mg of triacetin, being most preferred.

Tablet coating is designed to maintain structural integrity when exposed to the humid air and will not delay disintegration time significantly. This produces a stable dosage form.

The finished film coated tablets of the present invention typically have the following physical characteristics: Tablet Weight: 1100–1230 mg; Disintegration Time: Less than 30 minutes; Hardness: Greater than 60 SCUs; Thickness: 0.200"–0.400"; Friability: 0–0.1%/ 15 minutes. Preferably, these tablets have a tablet weight of approximately 1138 mg, a hardness of 70–80 SCUs, a thickness of approximately 0.375", and a friability of approximately 0%/15 minutes.

Povidone, a binder, is usually added during the wet granulation stage rather than the bulk drug stage, as is done in the present invention. This eliminates a rewetting/drying step which saves time arid money. While not intending to be limited by theory, it is believed that adding Povidone, according to the process of the current invention, may increase the cohesiveness of the colestipol hydrochloride molecules, which have two basic bonds, inter- and intra-forces. The addition of Povidone in the Colestipol hydrochloride manufacturing process may increase the cohesiveness of the inter- and intra-molecular bonds due to the nature of the polymeric structure. From about 10 to about 200 mg of Povidone may be used in the process of the current invention, with 40 mg being preferred.

Other pharmaceutical binders which will work in the process of the current invention include hydroxymethyl cellulose, hydroxyethyl cellulose and starch. However, Povidone is preferred.

Chart A shows the process of the current invention which utilizes a one-step drying method including wet granulation of the bulk drug. Chart B shows an alternate method of wet granulating the tablets which utilizes a two-step drying process similar to what is found in pharmaceutical manufacturing of granulated tablets. Tablets of the present invention were manufactured using both methods and it was found that Chart A is much more efficient than Chart B.

CHART A

Chart A describes the preferred method for preparing a film coated 1000 mg tablet of Colestipol hydrochloride.

The compounds A-1 and A-2 are polymerized and crosslinked according to the process described in U.S. Pat. No. 3,803,237, which is hereby incorporated by reference herein. Water is added to the resulting material at a ratio of 5 parts water to 1 part resulting material to a ratio of 12 parts water to 1 part resulting material to give a Colestipol hydrochloride slurry (A- 3). A ratio of 12 parts purified water USP to one part resulting material is preferred. The slurry is milled with a precision incremental cutting machine, such as a Comitrol mill to yield milled Colestipol hydrochloride slurry (A-4) having approximately 92% moisture. The milled slurry is dewatered to give milled dewatered Colestipol hydrochloride (A-5) having approximately 80% moisture. A binder Povidone USP K=30 is added to the milled dewatered Colestipol hydrochloride at a level of 4% to give milled, dewatered Colestipol hydrochloride with povidone (A-6). The wet granulated material is passed through a dryer, such as a Wyssmont Dryer or an Inox Vacuum Dryer, until loss on drying (LOD) is below 1% moisture to give dried milled Colestipol hydrochloride aggregates with povidone (A-7). The use of the Inox Vacuum Dryer is preferred. This material is then de, aggregated using a Micropulverizer with an 046 screen, or other suitable mill, such as a Comil, to break up any aggregate-clumps formed during drying. Colloidal Silicon Dioxide NF is added as a glidant and anti-caking agent, and Magnesium Stearate is added to lubricate the stock. The resulting material is compressed into a tablet using a D tooling press (8,000–10,000 lbs compressional force) to give compressed tablets (A-8).

A seal coating is placed on the tablet consisting of Cellulose Acetate Phthalate NF (CAP), which is dissolved in a mixture of Methylethyl Ketone (MEK) and S. D. Alcohol 3A Anhydrous, to give seal coated tablets (A-9). Triacetin USP is used as the plasticizer for the CAP solution. This sealing solution provides a barrier which allows the aqueous clear coating to be applied to the surface of the tablet without initiating disintegration of the tablet core upon contact.

An aqueous clear coating is placed on the tablet consisting of Hydroxypropyl Methylcellulose E5 Premium 2910 USP 5 CPS and 15 CPS to give clear coated tablets (A-10). The solids for the clear coating are dissolved in Purified Water USP, using Triacetin USP as the plasticizer. This clear coating gives the tablets the strength to withstand swelling from exposure to humid environmental conditions.

Finally, the tablet is waxed with Carnauba Wax NF #120 for ease in packaging to give a film coated 1000 mg tablet of Colestipol hydrochloride (A-11).

CHART B

Chart B describes an alternative method for preparing a film coated 1000 mg tablet of Colestipol hydrochloride of the present invention.

The compounds B-1 and B-2 are polymerized and crosslinked according to the process described in U.S. Pat. No. 3,803,237, which is hereby incorporated by reference herein. The resulting material is washed with water at a ratio of 8 parts Purified Water USP to one part resulting material and then dried to less than 1% moisture to give Colestipol hydrochloride USP (B-3). (See, e.g., the "bead process" disclosed in U.S. Pat. No. 3,803,237.) Water is added to the Colestipol hydrochloride USP at a ratio of 5 parts water to one part Colestipol hydrochloride USP to a ratio of 12 parts water to one part Colestipol hydrochloride USP. A ratio of 12 parts purified water USP to one part Colestipol hydrochloride USP is preferred. The Colestipol hydrochloride USP and water are then mixed to give Colestipol hydrochloride slurry (B4). The slurry is milled with a Comitrol mill to yield milled Colestipol hydrochloride slurry (B-5). This slurry is then dewatered with a Buchner funnel to yield milled, dewatered Colestipol hydrochloride (B-6). This material is then tray dried down to 20% moisture to give milled, semi-dried Colestipol hydrochloride (B-7). (See, e.g., the process disclosed in International Publication No. WO 89/12452, published 28 Dec. 1989.) This material is placed in the product container of a GLATT Fluid Bed Processor. Povidone solution is sprayed into the GLATT to produce Colestipol hydrochloride granules with Povidone (B-8). These granules are dried, in the GLATT, until the outlet temperature reaches approximately 60° C., producing dried milled, granulated, Colestipol hydrochloride Aggregates with Povidone (B-9). This material is then de, aggregated using a Micropulverizer with an 046 screen, or other suitable mill, such as a Comil, to break up any aggregate-clumps formed during drying. Colloidal Silicon Dioxide NF is added as a glidant and anti-caking agent, and Magnesium Stearate is added to lubricate the stock. The resulting material is compressed into a tablet using a Manesty Express with D tooling to yield compressed tablets (B-10).

The compressed tablets are seal coated (B-11), clear coated (B-12) and waxed, as described in Chart A above, to give film coated 1000 mg tablets of Colestipol hydrochloride (B-13).

Colestipol hydrochloride is a crosslinked polymer. The compound will swell to three to four time of its volume in the aqueous phase. If colestipol hydrochloride is compressed into a tablet without a binder, the tablet will not attain the hardness needed to withstand coating and shipping. Friability of such a tablet must be below 0.1% in 15 minutes and the tablet thickness must be less than 0.340". The tablets of the current invention, surprisingly and unexpectedly, have these advantageous properties as detailed in the examples below.

DESCRIPTION OF THE PREFERRED EMBODIMENTS

EXAMPLE 1

Colestipol Hydrochloride—1000 mg Tablet (Refer to Chart A)

1. Process A: 1) Slurry preparation (mixing—milling—dewater)

Slurry preparation:

| Colestipol hydrochloride beads | 300 Kg |
|---|---|
| Purified Water USP | 3600 Kg |

MIXING—In a suitable container, mix the above for about 30 min. to about 1 hour or until the mixture is hydrated.

MILLING—Pass the above mixture through a Comitrol 1700 mill.

DEWATER—Pass the milled material through a Sharple Centrifuge. Total yield after dewater approx 1620 Kg (82% moisture content)

2. Process B: PVP adding

PVP Solution Preparation:

| Povidone (PVP) | 12 Kg |
|---|---|
| Purified Water USP | 36 Kg |

PREPARATION: To a suitable container mix the above until solution is clear.

MIXING: To a Pony mixer, add 405 Kg milled dewatered Colestipol and 12 Kg Povidone Solution (25%). Mix for 5 minutes.

3. Process C: Drying

When using a Wyssmont Dryer, predry the material with the following parameters:

| 1) Inlet temperature | 230° F. |
|---|---|
| 2) Total feeding time | 12 hrs |
| 3) Outlet temperature | no reading |
| 4) Residence time | 3½ hrs |
| 5) Final moisture | 20% |

Then pass the material through #8 screen and dry under the following conditions:

| 1) Inlet temperature | 190° F. |
|---|---|
| 2) Total feeding time | 5 hrs |
| 3) Residence time | 1½ hrs |
| 4) Final moisture | 0.2% |
| 5) Water soluble content | 0.1% |

When using an Inox Vacuum Dryer, dry the material with the following parameters:

| 1) Inlet temperature | 120–160° C. |
|---|---|
| 2) Vacuum | 22–25 millibar |
| 3) Maintain product temperature at less than 50° C. | |
| 4) Endpoint loss on drying (LOD) is less than one percent (1%). | |

4. Process D: Deaggregation (micropulverizing)

Pass the batch through a micropulverizer (or other suitable deaggregation device) with herring bone shape screen size 046.

5. Process E: Mixing

To a 5 cu ft PK Blender add:

| Dried milled Colestipol hydrochloride | 50 Kg |
|---|---|
| Cab-o-sil | 250 g |
| Magnesium Stearate | 150 g |

Mix for 10 minutes and 3 minutes respectively.

6. Process F: Compressing

Compress the mixture from step 5 on a Manesty Express with Motrin 800 mg D tooling (0.7446"×0.378" special capsule elliptical), using a Compression force of 8,000–10,000 lbs.

The physical characteristics initially measured for the compressed tablets were typically as follows: (The figures are approximate)

| Disintegrating time (for 6 tablets) | 4 minutes 53 seconds |
|---|---|
| Tablet thickness | 0.327" |
| Tablet hardness | 43.7 SCUs |
| Tablet weight | 1046 mg |
| Friability | 0–0.1%/15 minutes |

7. Process G: Seal coating

| Per Tablet | | Per 100 Kg batch |
|---|---|---|
| 1048 mg | Compressed Tablet Cores | 103 Kg |
| 15.6 mg | Cellulose Acetate Phthalate NF | 1.544 Kg |
| 120 mg | Methyl Ethyl Ketone | 11.88 Kg |
| 120 mg | S.D. Alcohol 3A Anhydrous | 11.88 Kg |
| 3.12 mg | Triacetin USP | 308.9 g |

To a suitable container, mix the above ingredients until the solution is clear and lump free. Spray the solution on the batch with the Accela-Cota 48" by the following parameters:

| Inlet temperature | 15–30° C. |
|---|---|
| Exhaust temperature | |
| a. begin | Room Temperature |
| b. during | Room Temperature |
| Spray rate | 430 g/min |
| Airless (Graco) gun pressure | 20–40 lbs |
| Pan Speed | 5 RPM's |

8. Process H.: Clear Coating

| Per Tablet | | Per 100 Kg batch |
|---|---|---|
| 1066 mg | Sealcoated Colestid Tablets | 105 Kg |
| 30 mg | Hydroxypropylmethyl Cellulose E5 Premium 5 cps | 2.97 Kg |
| 30 mg | Hydroxypropylmethyl Cellulose 15 cps | 2.97 Kg |
| 12 mg | Triacetin USP | 1.188 Kg |
| 860 mg | Purified Water USP | 85.14 Kg |

Mix the above ingredients until solution is clear. Spray the solution on the tablets in Accela-Cota 48" according to the following parameters:

| 1. Inlet temperature | 80–85° C. |
|---|---|
| 2. Outlet temperature | |
| a. begin | 45° C. |
| b. during | 40–45° C. |
| 3. Air Atomization | |
| a. nozzle | 50 psi |
| b. cylinder | 70 psi |
| 4. Spray rate | 660 g/min |
| 5. Binks gun air spray system | 4 GUNS |
| 6. Disintegration time | NMT 10 min |

The physical characteristics of the final film coated tablets were typically as follows: (The figures are approximate)

| Weight: | 1138 mg |
|---|---|
| Disintegration Time: | less than 30 minutes |
| Hardness: | 60–80 SCUs |
| Thickness: | 0.375" |
| Friability: | 0%/15 minutes |

EXAMPLE 2

1000mg Colestid Tablets (Refer to Chart B)

Wet 7 kg of Colestipol hydrochloride USP with 84 Liters of Purified water USP in a suitable container and mix until dispersed. Using a Comitrol Mill, wet mill the Colestipol hydrochloride to achieve a reduced particle size. Dewater the milled slurry using a Buchner funnel and place on Trays to dry to 20% moisture. Using the following formula and methods, compress into a tablet which can be film coated:

| Colestipol hydrochloride, milled (20% moisture) | 7 Kg |
|---|---|

Granulation excipient preparation:

| PVP | 280 g |
|---|---|
| Water/ethanol, 1/1 | 1100 g |

Dissolve PVP into water/alcohol mixture with agitation. To the Product container, add the Colestipol hydrochloride. Granulate with the PVP solution according to the following parameters:

| Inlet temperature | 90° C. |
|---|---|
| Outlet temperature | 40° C. |
| Spray rate | 8–70 Gm/min |

Final dry to outlet temperature of at least 50° C.

Final mixing:

| Colestipol granules from above | 1 Kg |
|---|---|
| Ca-bo-sil | 5 g |
| Magnesium Stearate | 3 g |

Directions: Mix the above ingredients in a Hobart Mixer for 5 minutes.

Compress the mixture into tablet using a Manesty Express with D tooling, (0.7446"×0.378" special capsule elliptical) using a 8,000–10,000 lbs compressional force.

The physical characteristics initially measured for the compressed tablets were typically as follows: (The figures are approximate)

| Disintegration time: (6 tablets): | 5 minutes |
|---|---|
| Weight: | 1056 mg |
| Hardness: | 43.7 SCUs |
| Thickness: | 0.329" |
| Friability: | 0%/4 min.; <0.1%/15 min. |

The ingredients listed in Table 3 below are used to coat the tablets.

The following parameters are used to seal coating: (24" Accela-Cota)

| Inlet air temperature: | 15–30° C. |
|---|---|
| Outlet air temperature: | 15–30° C. |
| Airflow rate: nozzle: 30 | psi cylinder: 60 psi |
| Spray rate: | 20–35 RPM's |
| Pan Speed: | 12–20 RPM's |

The following parameters are used for the clear coating: (24" Accela-Cota)

| Inlet air temperature: | Adjust to maintain outlet air temperature |
|---|---|
| Outlet air temperature: | 40–50° C. |
| Air atomization pressure: nozzle: 30 | psi cylinder: 60 psi |
| Pan Speed: | 12–20 RPM's |
| Binks guns | 1 air Binks gun |

Wax the coated tablets with Carnauba wax NF for ease in handling.

The physical characteristics of the final film coated tablets are given in Example 1.

EXAMPLES 3–18

Failure of Other Tablets

The following examples demonstrate attempts at making a 1000 mg Colestid Tablet, which were unsuccessful for tableting and/or coating. The formulation used, the physical characteristics obtained, and in some examples, the process steps used, are given. These failures demonstrate the surprising and unexpected results achieved by the tablets and process of the current invention.

EXAMPLE 3

Formulation was as follows:

| Colestipol hydrochloride (milled) | 1 Kg |
|---|---|
| Magnesium Stearate | 5 g |

Weigh ingredients and mix well using a Hobart mixer.
Physical characteristics were as follows: (Kilian press)

| Weight: | 1005 mg |
|---|---|
| Disintegration: | 3" 55' |
| Hardness: | 41.2–44.1 |
| Thickness: | 342–372" |
| Friability: | 4.92814% |
| Pressure: | 4,400 lbs |
| Precomp. Pressure: | 400 lbs |

These tablets had friability and flow problems. With these tablets, it was not possible to achieve the desired tablet weight.

EXAMPLE 4

Excipients for granulation were as follows:

| Povidone k = 30 (PVP) | 300 g |
|---|---|
| S.D. Alcohol 3A Anhydrous | 2000 ml |

Formulation was as follows:

| Colestipol hydrochloride (milled) | 6 Kg |
|---|---|
| Silicon dioxide | — |
| Magnesium Stearate | 30 g |

Weigh all materials. Mix the excipients and granulate the Colestipol using the T.K. Fielder High Sheer Mixer/Granulator. Place granulation (wet) in the ovens at 120 degrees F. for 12–16 hours until dry. Lubricate with magnesium stearate. Compress on the Kilian press.

These tablets had friability and flow problems. With these tablets, it was not possible to achieve the desired tablet weight.

EXAMPLE 5

Formulation was as follows:

| Colestipol hydrochloride (milled) | 1 Kg |
|---|---|
| Magnesium Stearate | 3 g |
| Avicel PH 102 | 30 g |

Physical characteristics were as follows: (Kilian press)

| Weight: | 1030 mg |
|---|---|
| Friability: | 0.149% (poor) |

These were soft tablets which had poor friability and flow.

EXAMPLE 6

Formulation was as follows:

| Colestipol hydrochloride (milled) | 1 Kg |
|---|---|
| Magnesium Stearate | 2.5 g |

Physical characteristics were as follows: (Kilian Press)

| Weight: | 1002.5 mg |
|---|---|
| Friability: | 0.97% |

These tablets were not hard enough for coating pan due to poor friability.

EXAMPLE 7

Formulation was as follows:

| Colestipol hydrochloride (milled) | 5 Kg |
|---|---|
| Granulation excipient: | |
| Povidone (PVP) | 300 g |
| Purified Water USP | 2000 ml |

Mix PVP and water until clear. Weigh 5 Kg of Colestipol hydrochloride. Heat Glatt Fluid Bed Dryer until reaches 50 degrees (going left to right on the panel) (Shaking Intervals every 30 seconds for a length of 5 seconds)

| Inlet temperature: | 70° C. |
|---|---|
| Exhaust temperature: | 32° C. |
| Exhaust Air Flap: | 40% |

Adjust spray ratio to keep product from sticking to sides and filter.

The granulation was difficult to dry unless alcohol was used as a granulating agent.

EXAMPLE 8

Formulation was as follows:

| Colestipol hydrochloride (milled) | 1 Kg |
|---|---|
| Magnesium Stearate | 6 g |
| Avicel PH 102 | 100 g |

Physical characteristics were as follows: (Kilian Press)

| Theory Weight: | 1100 mg |
|---|---|
| Actual Weight: | 650 mg |
| Hardness: | 42.5 |
| Pressure: | 4000 lbs |
| Precomp: | 500 lbs |
| Friability: | Not measured |

With these tablets, it was not possible to achieve the desired tablet weight.

EXAMPLE 9

Formulation was as follows:

| Colestipol hydrochloride (milled) | 1 Kg |
|---|---|
| Magnesium Stearate | 6 g |
| Avicel PH 102 | 10 g |

Screen materials and mix in a Hobart mixer.
Physical characteristics are as follows:

| Weight: | 1016 mg |
|---|---|
| Hardness: | 26–29 SCU's |
| Friability: | 0.128% (poor) |
| Pressure: | 2,000–4,100 lbs |
| Precomp: | 300–800 lbs |

There was a friability problem because the tablets were too soft.

EXAMPLE 10

Formulation was as follows:

| Colestipol hydrochloride (milled) | 1 Kg |
|---|---|
| Avicel PH 102 | 50 g |
| Magnesium Stearate | 2.5 g |

Mix materials.
Physical characteristics were as follows:

| Weight: | 1052.5 mg |
|---|---|
| Hardness: | 33–34 SCU's |
| Friability: | 0.118% (poor) |
| Pressure: | 4,000 lbs |
| Precomp: | 500 lbs |

The friability of these tablets was not good because the tablets were too soft.

EXAMPLE 11

Formulation was as follows:

| Colestipol hydrochloride (milled) | 800 g |
|---|---|
| Avicel PH 102 | 76 g |
| Mg stearate | 5 g |

Physical characteristics were as follows: (Kilian Press)

| Weight: | 1105 mg |
|---|---|
| Friability: | Not measurable |

These tablets were too soft, like a sponge, due to moisture in the Colestipol material.

EXAMPLE 12

Formulation was as follows:

| Colestipol hydrochloride (milled) | 1 Kg |
|---|---|
| Avicel PH 102 | 150 g |
| Magnesium Stearate | 6 g |

Physical characteristics were as follows: (Kilian Press)

| Weight: | 1156 mg |
|---|---|
| Hardness: | 36–44 SCU's |
| Friability: | Poor |
| Pressure: | 4,400 lbs |
| Precomp: | 550 lbs |

Friability of these tablets was not good enough to withstand a coating pan.

EXAMPLE 13

Formulation was as follows:

| Colestipol hydrochloride (milled) | 700 g |
|---|---|
| Magnesium Stearate | 4 g |
| Avicel PH 102 | 70 g |

Physical characteristics were as follows:

| Weight: | 1050 mg |
|---|---|
| Hardness: | 33.2 SCU's |
| Friability: | Poor |

EXAMPLE 14

Formulation was as follows:

| Colestipol hydrochloride (milled) | 1 Kg |
|---|---|
| Magnesium Stearate | 6 g |
| Avicel PH 102 | 100 g |

Physical characteristics were as follows:

| Weight: | 1100 mg |
|---|---|
| Hardness: | 42.2–42.7 SCU's |
| Friability: | 0.53% |

EXAMPLE 15

Formulation was as follows: (Kilian Press)

| Colestipol hydrochloride (milled) | 940 gm |
|---|---|
| Povidone (PVP) | 60 g |
| Magnesium Stearate | 2.5 g |
| Cab-o-sil | 4 g |

Physical characteristics were as follows:

| Weight: | 1006 mg |
|---|---|

The flow of these tablets was poor.

EXAMPLE 16

Formulation was as follows:

| Colestipol hydrochloride (milled) | 1000 g |
|---|---|
| Povidone (PVP) | 50 g |
| Cab-o-sil | 5 g |
| Magnesium Stearate | 3 g |

Physical characteristics were as follows: (Kilian Press)

| | |
|---|---|
| Weight: | 1058 mg |
| Disintegration: | 5" |
| Hardness: | 40 SCU's |
| Thickness: | 0.347" |
| Friability: | Average |

EXAMPLE 17

Formulation was as follows:

| | |
|---|---|
| Colestipol hydrochloride (milled) | 1000 g |
| HPMC 5 CPS | 50 g |
| Avicel PH 102 | 50 g |
| Magnesium Stearate | 3 g |

Physical characteristics were as follows:

| | |
|---|---|
| Weight: | 1103 mg |
| Thickness: | 0.356" |
| Friability: | Poor |

EXAMPLE 18

Formulation was as follows:

| | |
|---|---|
| Colestipol hydrochloride (milled) | 1000 g |
| Povidone (PVP) | 4% |
| Chilsonator | 1000 lbs with a #8 screen |

Chilsonate and fitzmill. Compress to weight.
Physical characteristics were as follows:

| | |
|---|---|
| Weight: | 1040 mg |
| Hardness: | 37–40 SCU's |
| Thickness: | 0.346" |
| Friability: | Poor |

TABLE 1

| | Compressed Tablets of the Current Invention | Prior Art Compressed Tablets |
|---|---|---|
| Tablet size | 0.753" × 0.382" × 0.330" | 0.760" × 0.387" × 0.373" |
| Tablet hardness | >40 SCUs | <40 SCUs |
| Friability | 0–0.1%/15 minutes | 0.4% |
| Disintegration time | Less than 5 minutes | 6 minutes, 50 seconds |

TABLE 2

| Process of the Current Invention | Prior Art Process |
|---|---|
| Wet Granulation method used in bulk drug manufacture to add the binder Povidone One step drying by Wyssmont Dryer or Inox Vacuum Dryer | Direct compressing of tablet excipients Two step drying by tray dryer |

TABLE 3

Ingredients Used to Coat Tablets (Example 2)

| PER TABLET | | PER 10 Kg OF TABLETS |
|---|---|---|
| 15.6 mg | Cellulose Acetate Phthalate | 163 g |
| 120 mg | Acetone or Methylethyl Ketone | 1.26 kg |
| 3.12 mg | Triacetin USP | 32.7 g |
| 120 mg | S.D. Alcohol 3A Anhydrous | 1.26 kg |
| 30 mg | HPMC E5 PREMIUM 5 CPS | 314 g |
| 30 mg | HPMC 15 CPS | 314 g |
| 12 mg | Triacetin USP | 125.8 g |
| 860 mg | Purified Water USP | 9 kg |

CHART A

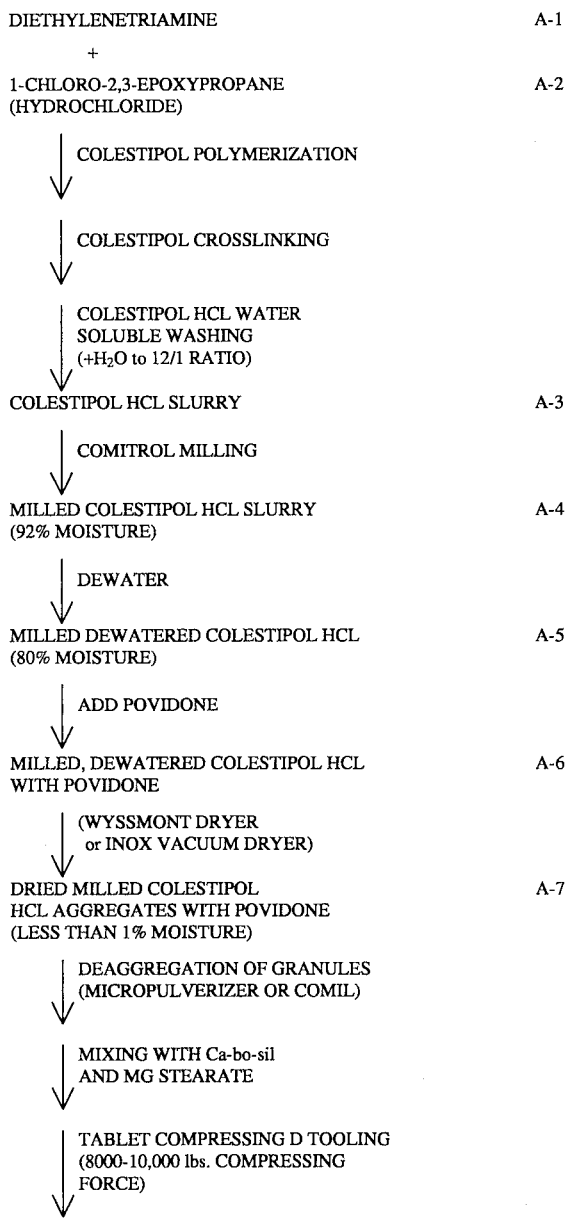

| | |
|---|---|
| DIETHYLENETRIAMINE | A-1 |
| + | |
| 1-CHLORO-2,3-EPOXYPROPANE (HYDROCHLORIDE) | A-2 |
| ↓ COLESTIPOL POLYMERIZATION | |
| ↓ COLESTIPOL CROSSLINKING | |
| COLESTIPOL HCL WATER SOLUBLE WASHING (+H$_2$O to 12/1 RATIO) | |
| ↓ COLESTIPOL HCL SLURRY | A-3 |
| ↓ COMITROL MILLING | |
| MILLED COLESTIPOL HCL SLURRY (92% MOISTURE) | A-4 |
| ↓ DEWATER | |
| MILLED DEWATERED COLESTIPOL HCL (80% MOISTURE) | A-5 |
| ↓ ADD POVIDONE | |
| MILLED, DEWATERED COLESTIPOL HCL WITH POVIDONE | A-6 |
| ↓ (WYSSMONT DRYER or INOX VACUUM DRYER) | |
| DRIED MILLED COLESTIPOL HCL AGGREGATES WITH POVIDONE (LESS THAN 1% MOISTURE) | A-7 |
| ↓ DEAGGREGATION OF GRANULES (MICROPULVERIZER OR COMIL) | |
| ↓ MIXING WITH Ca-bo-sil AND MG STEARATE | |
| ↓ TABLET COMPRESSING D TOOLING (8000-10,000 lbs. COMPRESSING FORCE) | |

CHART A -continued

| | |
|---|---|
| COMPRESSED TABLETS | A-8 |
| ↓ SEAL COATING (CAP/SD ALCOHOL 3A ANHYDROUS + MEK) | |
| SEAL COATED TABLETS | A-9 |
| ↓ CLEAR COATING (AQUEOUS/HPMC) | |
| CLEAR COATED TABLETS | A-10 |
| ↓ WAXING (CARNAUBA WAX) | |
| FILM COATED TABLETS | A-11 |

CHART B

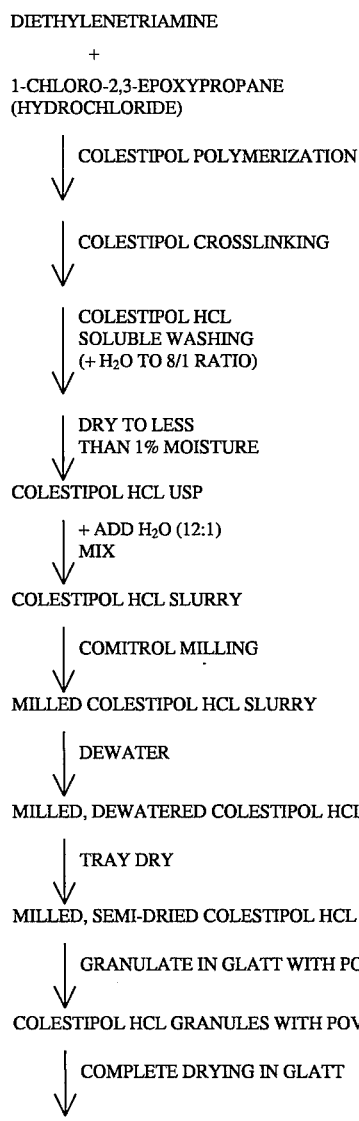

| | |
|---|---|
| DIETHYLENETRIAMINE + | B-1 |
| 1-CHLORO-2,3-EPOXYPROPANE (HYDROCHLORIDE) | B-2 |
| ↓ COLESTIPOL POLYMERIZATION | |
| ↓ COLESTIPOL CROSSLINKING | |
| ↓ COLESTIPOL HCL SOLUBLE WASHING (+ H₂O TO 8/1 RATIO) | |
| ↓ DRY TO LESS THAN 1% MOISTURE | |
| COLESTIPOL HCL USP | B-3 |
| ↓ + ADD H₂O (12:1) MIX | |
| COLESTIPOL HCL SLURRY | B-4 |
| ↓ COMITROL MILLING | |
| MILLED COLESTIPOL HCL SLURRY | B-5 |
| ↓ DEWATER | |
| MILLED, DEWATERED COLESTIPOL HCL | B-6 |
| ↓ TRAY DRY | |
| MILLED, SEMI-DRIED COLESTIPOL HCL | B-7 |
| ↓ GRANULATE IN GLATT WITH POVIDONE | |
| COLESTIPOL HCL GRANULES WITH POVIDONE | B-8 |
| ↓ COMPLETE DRYING IN GLATT | |

CHART B -continued

| | |
|---|---|
| DRIED, MILLED, GRANULATED, COLESTIPOL HCL AGGREGATES WITH POVIDONE. | B-9 |
| ↓ DEAGGREGATION OF GRANULES (MICROPULVERIZER OR COMIL) | |
| ↓ MIXING WITH CAB-O-SIL + MAGNESIUM STEARATE | |
| ↓ COMPRESS (MANESTY EXPRESS) | |
| COMPRESSED TABLETS | B-10 |
| ↓ SEAL COATING (CAP/SD ALCOHOL 3A ANHYDROUS + MEK) | |
| SEAL COATED TABLETS | B-11 |
| ↓ CLEAR COATING (AQUEOUS/HPMC) | |
| CLEAR COATED TABLETS | B-12 |
| ↓ WAXING (CARNAUBA WAX) | |
| FILM COATED TABLETS | B-13 |

We claim:

1. A pharmaceutical tablet which comprises approximately 1000 mg of fine-milled colestipol hydrochloride, 10–200 mg of povidone, 1–50 mg of colloidal silicon dioxide and 1–30 mg of magnesium stearate, and which has the following physical characteristics:

| | |
|---|---|
| Hardness: | Greater than 40 SCU's |
| Friability: | 0–0.1%/15 minutes. |

2. The tablet of claim 1, which has the following additional characteristics:

| | |
|---|---|
| Hardness: | 40–75 SCUs |
| Tablet Weight: | 1017–1079 mg |
| Disintegration Time: | Less than 5 minutes |
| Thickness: | 5.08–8.64 mm (0.200–0.340 inch). |

3. The tablet of claim 2, comprising approximately 1000 mg colestipol hydrochloride, wherein the tablet weight is approximately 1048 mg, the hardness is 40–50 SCUs, and the thickness is 8.13–8.64 mm (0.320–0.340 inch).

4. The tablet of claim 1, which comprises approximately 40 mg povidone.

5. The tablet of claim 1 comprising 40–50 mg povidone, 5–10 mg colloidal silicon dioxide, and 2.5–3.5 mg magnesium stearate.

6. The tablet of claim 5, comprising approximately 40 mg povidone, approximately 5 mg colloidal silicon dioxide and approximately 3 mg magnesium stearate.

7. The tablet of claim 1, which further has a seal coating comprising cellulose acetate phthalate and triacetin in the coating.

8. The tablet of claim 7, comprising 2–100 mg cellulose acetate phthalate and 0.5–20 mg triacetin in the coating.

9. The tablet of claim 8, comprising approximately 15.6 mg cellulose acetate phthalate and approximately 3.12 mg triacetin in the coating.

10. The tablet of claim 7, which further has a clear coating comprising hydroxypropyl methylcellulose and triacetin in the coating.

11. The tablet of claim 10, comprising 5–100 mg hydroxypropyl methylcellulose 2910 E5 Premium USP 5 CPS, 5–100 mg hydroxypropyl methylcellulose 2910 USP 15 CPS and 2–80 mg triacetin in the coating.

12. The tablet of claim 11, comprising approximately 30 mg hydroxypropyl methylcellulose 2910 E5 Premium USP 5 CPS, approximately 30 mg hydroxypropyl methylcellulose 2910 USP 15 CPS and approximately 12 mg triacetin in the coating.

13. The tablet of claim 12, which has the following physical characteristics:

| | |
|---|---|
| Tablet Weight: | 1100–1230 mg |
| Disintegration Time: | Less than 30 minutes |
| Hardness: | Greater than 60 SCUs |
| Thickness: | 5.08–10.16 mm (0.200–0.400 inch) |
| Friability: | 0–0.1%/15 minutes. |

14. The tablet of claim 13, wherein the tablet weight is approximately 1138 mg, the hardness is 60–80 SCUs, the thickness is approximately 9.52 mm (0.375 inch) and the friability is approximately 0%/15 minutes.

15. The tablet of claim 1, obtainable by adding 10–200 mg. providone to a dewatered slurry of fine-milled colestipol hydrochloride; drying the resultant mixture; deaggregating the dried material; adding 1–50 mg. of colloidal silicon dioxide and 1–30 mg. of magnesium stearate to the deaggregated material; and compressing the resultant mixture into a tablet.

16. A process for preparing the tablet of claim 1, which comprises the steps of adding 10–200 mg. providone to a dewatered slurry of fine-milled colestipol hydrochloride; drying the resultant mixture; deaggregating the dried material; adding 1–50 mg. of colloidal silicon dioxide and 1–30 mg of magnesium stearate to the deaggregated material; and compressing the resultant mixture into a tablet.

17. The process of claim 16 wherein the resultant mixture is compressed into a tablet using 8,000–10,000 lbs. compressional force.

* * * * *